United States Patent [19]
Yoshida

[11] Patent Number: 5,885,224
[45] Date of Patent: Mar. 23, 1999

[54] INTRAOCULAR SUBSTANCE MEASURING APPARATUS

[76] Inventor: Akitoshi Yoshida, 5-8, 6-chome, Kaguraoka 4-jo, Asahikawa-shi, Hokkaido, Japan, 078

[21] Appl. No.: 741,282

[22] Filed: Oct. 30, 1996

[30] Foreign Application Priority Data

Oct. 31, 1995 [JP] Japan .................................. 7-308232

[51] Int. Cl.⁶ .............................................. A61B 13/00
[52] U.S. Cl. ........................................................ 600/558
[58] Field of Search .................................. 600/318, 321, 600/558; 351/221

[56] References Cited

U.S. PATENT DOCUMENTS

| | | | |
|---|---|---|---|
| 5,058,596 | 10/1991 | Makino et al. | 600/558 |
| 5,258,788 | 11/1993 | Furuya | 600/318 |
| 5,553,617 | 9/1996 | Barkenhagen | 600/558 |

FOREIGN PATENT DOCUMENTS

| | | |
|---|---|---|
| 261 957 A1 | 11/1988 | Germany . |
| 43 21 796 A1 | 1/1994 | Germany . |
| 42 43 142 A1 | 6/1994 | Germany . |
| WO 87/03188 | 6/1987 | WIPO . |

OTHER PUBLICATIONS

"A Scanning Ocular Spectrofluorophotometer", Investigative Ophthamology & Visual Science, vol.29, No. 8, Aug. 1988, pp. 1285–1293, J.W. McLaren et al.

*Primary Examiner*—Max Hindenburg
*Attorney, Agent, or Firm*—Nikaido, Marmelstein, Murray & Oram

[57] ABSTRACT

The direction of an optical axis of an excitation optical system is so set that the same intersects with an optical axis of a photoreceiving optical system on a cornea and an excitation light beam is not incident upon a crystalline lens through a pupil. The photoreceiving optical system comprises a one-dimensional solid-state image pickup device as a photodetector, and a slit is arranged on a light incidence side of the one-dimensional solid-state image pickup device for distinguishing measuring light generated from the cornea from that generated from other eyeball portions and introducing the same into the one-dimensional solid-state image pickup device. Raman scattered light or fluorescence generated from the cornea can be detected by that of photo-electric conversion elements of the one-dimensional solid-state image pickup device positioned on the optical axis of the photoreceiving optical system, so that an intraocular substance is obtained on the basis of its detected value.

50 Claims, 13 Drawing Sheets

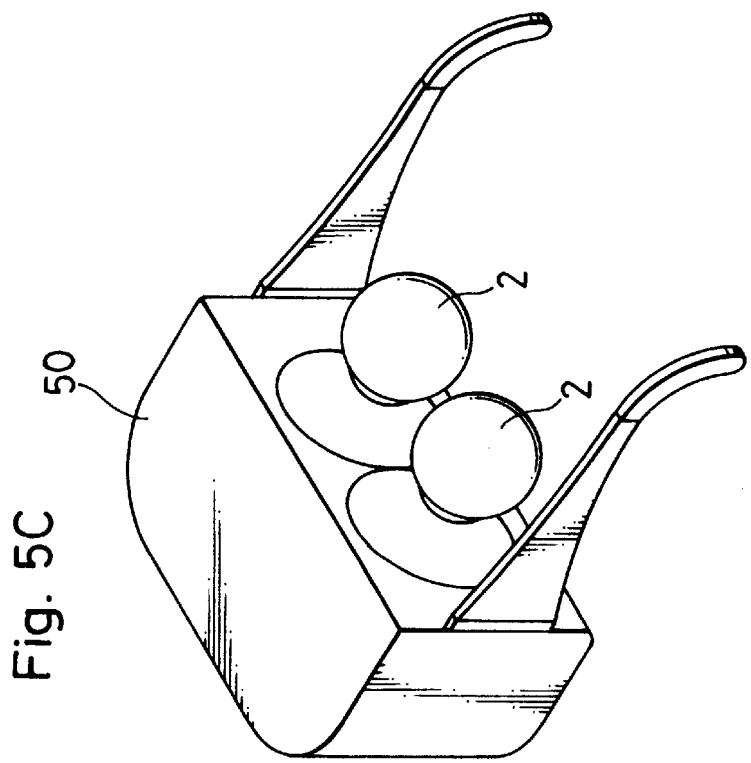
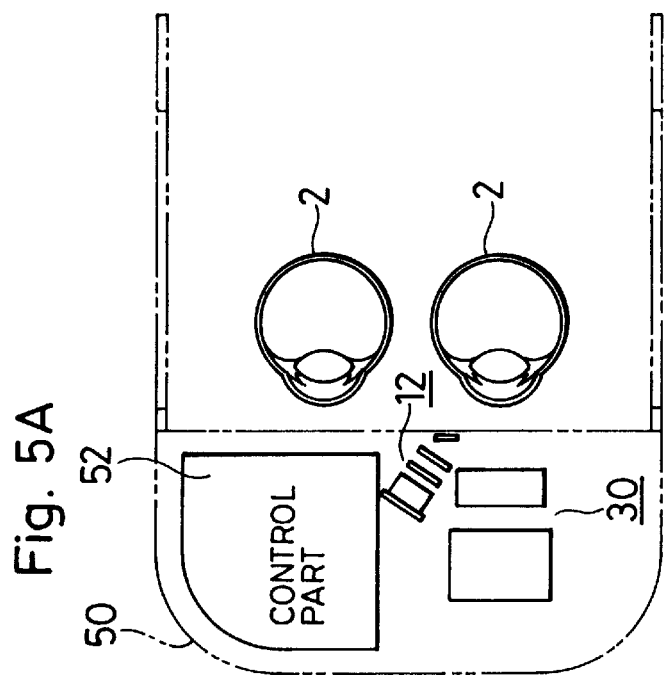
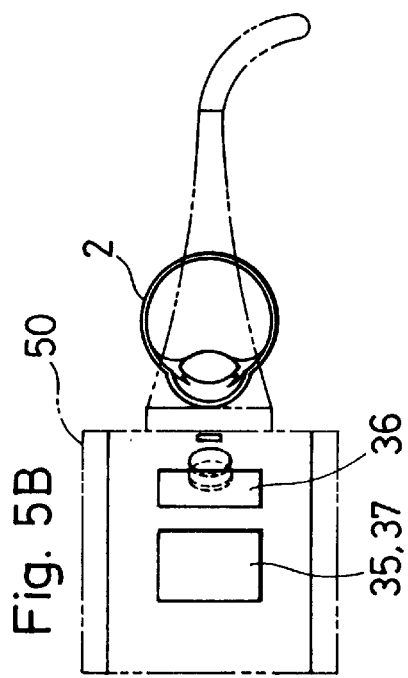

INTRAOCULAR SUBSTANCE MEASURING APPARATUS

BACKGROUND OF THE INVENTION

1. Field of the Invention

The present invention relates to an apparatus for measuring intraocular substances by irradiating an eyeball with a monochromated or single-wavelength excitation light beam in the visible to near infrared regions from an excitation optical system and detecting measuring light including at least one of scattered light and fluorescence generated from the eyeball by a photoreceiving optical system.

2. Description of the Background Art

Vitreous fluorophotometry (VFP) is performed as an examination of quantitatively testing the function of a blood-ocular barrier by measuring intraocular fluorescence as a method of irradiating the eyeball with excitation light and obtaining information from scattered light or fluorescence from the eyeball.

In order to diagnose diabetes mellitus or judge necessity for insulin administration, blood-sugar level must be measured. Although a method of collecting blood for measuring the blood-sugar level is correct, this causes the patient pain, and the examination is troublesome and requires a long time.

Therefore, various methods of noninvasively measuring intraocular substances on the basis of optical information from eyeballs are studied. For example, methods of irradiating eyeballs with excitation light and measuring the blood-sugar levels on the basis of information obtained therefrom are studied. One of such methods is a method of irradiating the crystalline lens with excitation light, receiving back-scattered light thereof, separating the same into fluorescence and Rayleigh light through a spectroscope or a dichroic beam splitter, obtaining information allowing diagnosis of diabetes mellitus from a value obtained by normalizing the fluorescence intensity with the Rayleigh light intensity, and diagnosing diabetes mellitus, cataract or still another disease on the basis thereof (refer to U.S. Pat. No. 5,203,328).

In another method, infrared absorption by the crystalline lens or the refractive index of visible light is measured for obtaining the blood-sugar level in the crystalline lens on the basis thereof (refer to Japanese Patent Laying-Open Gazette No. 51-75498 (1986)). In still another method, aqueous humor filling up a clearance between the cornea and the crystalline lens is irradiated with plane polarized light so that the blood-sugar level is obtained by measuring the angle of rotation of the polarization axis or the refractive index (refer to U.S. Pat. No. 3,963,019).

A method of obtaining a cholesterol value as another vital substance is also proposed. In this method, aqueous humor is irradiated with excitation light, so that the intensity of scattered light therefrom or the mobility of protein which is a scatterer is measured for obtaining the cholesterol value (refer to U.S. Pat. No. 4,836,207).

In the methods heretofore studied, information from vitreous bodies, crystalline lenses, aqueous humor etc. of the eyeballs play central roles. However, the inventor has discovered that information from the cornea has a specific property which cannot be obtained from information from other portions of the eyeball (refer to 19th Corneal Conference, Program, Abstracts, 122 "Influence of Blood-Sugar Level Change Exerted on Corneal Natural Fluorescence on Sufferer from Diabetic Retinopathy" and Abstract of "Clinical & Epidemiologic Research, Electrophysiology, Physiology & Pharmacology, Retina" Meeting (No. 2208-175)).

SUMMARY OF THE INVENTION

Accordingly, an object of the present invention is to provide an apparatus for measuring various intraocular substances which are effective for diagnosis of diseases by selectively fetching optical information from the cornea.

The measuring apparatus according to the present invention comprises an excitation optical system which is arranged in such a positional relation that an excitation light beam is incident not upon a crystalline lens but upon a cornea in a state of fixing an eyeball to a prescribed measuring position while fixing its ocular axis in a measuring direction, and a photoreceiving optical system having an optical axis which is spatially different from an optical axis of the excitation optical system and comprising an optical device for guiding measuring light which is generated from the cornea while distinguishing the measuring light from that generated from other eyeball parts, and a photodetector for detecting the measuring light which is guided by the optical device, for irradiating the cornea with the excitation light beam from the excitation optical system and detecting measuring light which is generated from the cornea by the photoreceiving optical system thereby measuring intraocular substances.

The photoreceiving optical system preferably further comprises spectroscopic means for separating the measuring light generated from the eyeball into its spectral components. The spectroscopic means is provided between the optical device for guiding the measuring light generated from the cornea while distinguishing the same from that generated from other eyeball portions and the photodetector, for example, while the photodetector is so arranged as to detect the measuring light which is separated into its spectral components by the spectroscopic means. If the spectroscopic means is not of a wavelength dispersion type, the spectroscopic means can alternatively be arranged on a light incidence side of the aforementioned optical device.

In order to fix the ocular axis in a specific direction such as the optical axis direction of the photoreceiving optical system or a direction keeping a constant angle with the optical axis direction, for example, the apparatus preferably further comprises an ocular axis fixing optical system comprising an ocular axis fixing light source for generating visible light independently of the light source of the excitation optical system and introducing a light beam from this light source into the eyeball.

The ocular axis fixing optical system may alternatively be provided on the eyeball side whose intraocular substances are to be measured, or on another eyeball side whose intraocular substances are not measured.

If the ocular axis is not fixed, it is preferable that measurement can be performed when the ocular axis is in a prescribed direction suitable for the measurement. Thus, a two-dimensional solid-state image pickup device such as a CCD solid-state image pickup device may be provided as a monitor for observing the direction of the eyeball for incorporating an output of the photodetector of the photoreceiving optical system while monitoring the direction of the eyeball with the two-dimensional solid-state image pickup device.

According to the present invention, the excitation optical system is so arranged that the excitation light beam is not incident upon the crystalline lens. In case of introducing the excitation light beam so that the optical axis of the excitation optical system intersects with the ocular axis on the cornea in a state of fixing the eyeball to the prescribed measuring position while fixing the ocular axis in the measuring direction, it is preferable to set the angle for intersecting with the ocular axis at about 40° to 90°, so that the incident light beam is not incident upon the crystalline lens through the pupil. The size of the pupil has individual variation and hence the lower limit value of about 40° of the angle varies with the subject, while it means the lower limit angle for preventing the excitation light beam from entering the crystalline lens.

Every one of a single photoelectric conversion element, a one-dimensional solid-state image pickup device such as a CCD sensor or a photodiode array, and a two-dimensional solid-state image pickup device such as a CCD solid-state image pickup device can be employed as the photodetector of the photoreceiving optical system.

When the photodetector is formed by a one-dimensional solid-state image pickup device, this one-dimensional solid-state image pickup device is preferably arranged so that photoelectric conversion elements are arranged along a straight line forming a prescribed angle with the optical axis of the photoreceiving optical system in a plane including the optical axis of the excitation optical system and the optical axis of the photoreceiving optical system, whereby it is possible to associate a position where the plane including the optical axes of the excitation and photoreceiving optical systems intersects with the eyeball with positions of the photoelectric conversion elements of the one-dimensional solid-state image pickup device by the optical device for guiding the measuring light generated from the cornea while distinguishing the measuring light from that generated from other eyeball portions.

Such an optical device can be formed by a slit, an optical fiber lens array or a lens. The slit can be implemented by arranging a plurality of thin plates which have a direction parallel to the optical axis of the photoreceiving optical system and perpendicular to the plane including the optical axes of the excitation and photoreceiving optical systems, in a direction perpendicular to the optical axis of the photoreceiving optical system in the plane including the optical axes of the excitation and photoreceiving optical systems. The optical fiber lens array, which is also called a condensing rod lens array or a Selfoc lens array, is prepared by arranging an optical fiber member in parallel with the optical axis of the photoreceiving optical system in the direction perpendicular to the optical axis of the photoreceiving optical system in the plane including the optical axes of the excitation and photoreceiving optical systems. The lens is adapted to form an image on the cornea in the vicinity of the ocular axis on the photodetector.

In this case, the spectroscopic means must be capable of separating the light into its spectral components while maintaining the correspondence between the position on the eyeball and the positions of the photoelectric conversion elements of the one-dimensional solid-state image pickup device, and an FT (Fourier transform spectroscope), a filter or an AOTF (acousto-optical tunable filter) can be employed as such spectroscopic means, to be arranged between the one-dimensional solid-state image pickup device and the optical device.

When the photodetector is formed by the one-dimensional solid-state image pickup device, it is possible to associate the incident light with the position on the eyeball by the optical device provided on its incidence side for identifying from which part of the eyeball the information is, whereby the intraocular substances can be more correctly measured.

When the photodetector is formed by the one-dimensional solid-state image pickup device and receives only light generated from a point where the optical axes of the excitation and photoreceiving optical systems intersect with each other on the cornea, it is possible to form a polychrometer which can simultaneously detect separated multiple wavelengths by combining an FT, an AOTF or a diffraction grating with the one-dimensional solid-state image pickup device and wavelength-dispersing measuring light from the point in the arrangement direction of the photoelectric conversion elements of the one-dimensional solid-state image pickup device.

When the photodetector is formed by a single photoelectric conversion element, a photodiode can be employed as the photodetector. In this case, the photoreceiving optical system is provided with an optical device for introducing only the light generated from the point where the optical axes of the excitation and photoreceiving optical systems intersect with each other on the cornea into the photodetector. Such an optical device can be formed by a slit, an optical fiber lens array or a lens. A dispersion type diffraction grating can also be employed as the spectroscopic means, as well as an FT, a filter and an AOTF.

When the photodetector is formed by a two-dimensional solid-state image pickup device, the optical device of the photoreceiving optical system can associate the position where the plane including the optical axes of the excitation and photoreceiving optical systems intersects with the eyeball with a position on a line of photoelectric conversion element arrangement of the two-dimensional solid-state image pickup device. Such an optical device can also be formed by a slit, an optical fiber lens array or a lens. In this case, the spectroscopic means can be formed by a multichannel spectroscope for wavelength- dispersing the light in a direction perpendicular to the photoelectric conversion element arrangement and separating the same into its spectral components, so that measuring light beams generated from a plurality of positions on the eyeball can be independently separated into spectral components thereof and detected.

When the photodetector is formed by the two-dimensional solid-state image pickup device, further, the same can also serve as a monitor for observing the direction of the eyeball while detecting the measuring light generated from the eyeball.

The excitation light beam which is applied from the excitation optical system to the eyeball is a monochromated or single-wavelength beam in the visible to near-infrared regions. An exemplary excitation optical system generating such an excitation light beam comprises a light source of an incandescent lamp generating excitation light of a continuous wavelength such as a tungsten lamp or a halogen lamp, and wavelength selection means such as a filter for monochromating the light from the light source. When the excitation light is converted to a parallel beam along the optical axis of the excitation optical system, the excitation optical system further comprises a slit.

Another exemplary excitation optical system comprises a laser unit for generating single-wavelength excitation light in the visible to near-infrared regions as a light source. When a semiconductor laser is used as the laser unit, the beam diverges and hence a lens or a slit is necessary for converting the excitation light to a parallel beam along the optical axis of the excitation optical system. When the semiconductor laser oscillates a plurality of wavelength light components, wavelength selection means such as an optical filter for selecting specific wavelength light is necessary.

When received light is Raman scattered light or fluorescence and the excitation light beam is monochromatic or single-wavelength light, data processing is simplified. When the excitation light is prepared from near infrared light, the eye makes no pupillary reaction and hence it is not necessary to administrate a mydriatic, and the measurement is simplified. It is convenient for measuring a small part of the cornea or performing area integration to convert the excitation light beam to a parallel beam.

When the excitation light beam is applied to only a point of the cornea, a condenser lens for condensing the excitation light on the cornea may be provided on the excitation optical system.

When a beam splitter is provided on the optical axis of the excitation light beam of the excitation optical system and part of excitation light fetched by the beam splitter is incident upon a partial photoelectric conversion element of the photodetector or another photodetector so that an output of the photodetector receiving the measuring light from the eyeball is corrected by an output of the photoelectric conversion element or the photodetector, it is possible to correctly measure scattered light or fluorescence even if there is fluctuation of the excitation light.

The excitation and photoreceiving optical systems can be integrally stored in a goggle structure which can be attached to a face, and the measurement can be readily performed in this case.

The goggle structure can be further provided with a transmission circuit which can output information including data measured by the photoreceiving optical system to an external data processor. The transmission circuit for transmitting the measured data can be implemented by any one of various means such as wireless, wire and optical pulse means.

The first measured intraocular substance is sugar, and determination can be made for glucose through a Raman scattering peak at 420 to 1500 $cm^{-1}$ or 2850 to 3000 $cm^{-1}$, preferably at 420 to 450 $cm^{-1}$, 460 to 550 $cm^{-1}$, 750 to 800 $cm^{-1}$, 850 to 940 $cm^{-1}$, 1000 to 1090 $cm^{-1}$, 1090 to 1170 $cm^{-1}$, 1200 to 1300 $cm^{-1}$, 1300 to 1390 $cm^{-1}$, 1450 to 1500 $cm^{-1}$ or 2850 to 3000 $cm^{-1}$ in a shift wavenumber from an excitation wavelength. Glucose (grape sugar), which is also called blood sugar, gives most important information for diagnosing diabetes mellitus or recognizing transition of the condition of a disease.

Another sugar can also be measured. With respect to inositol, for example, determination can be made through a Raman scattering peak at 400 to 1500 $cm^{-1}$ or 2900 to 3050 $cm^{-1}$, preferably at 400 to 500 $cm^{-1}$, 700 to 900 $cm^{-1}$, 1000 to 1100 $cm^{-1}$, 1200 to 1500 $cm^{-1}$ or 2900 to 3050 $cm^{-1}$ in a shift wavenumber from the excitation wavelength.

With respect to fructose, determination can be made through a Raman scattering peak at 550 to 1500 $cm^{-1}$ or 2900 to 3050 $cm^{-1}$, preferably at 550 to 620 $cm^{-1}$, 650 to 700 $cm^{-1}$, 780 to 870 $cm^{-1}$, 900 to 980 $cm^{-1}$, 1000 to 1150 $cm^{-1}$, 1200 to 1300 $cm^{-1}$, 1400 to 1480 $cm^{-1}$ or 2900 to 3050 $cm^{-1}$ in a shift wavenumber from the excitation wavelength.

With respect to galactose, determination can be made through a Raman scattering peak at 400 to 1500 $cm^{-1}$ or 2850 to 3050 $cm^{-1}$, preferably at 450 to 550 $cm^{-1}$, 630 to 900 $cm^{-1}$, 1000 to 1180 $cm^{-1}$, 1200 to 1290 $cm^{-1}$, 1300 to 1380 $cm^{-1}$, 1400 to 1500 $cm^{-1}$ or 2850 to 3050 $cm^{-1}$ in a shift wavenumber from the excitation wavelength.

With respect to sorbitol, determination can be made through a Raman scattering peak at 380 to 1500 $cm^{-1}$ or 2700 to 2960 $cm^{-1}$, preferably at 388 to 488 $cm^{-1}$, 749 to 862 $cm^{-1}$, 933 to 1120 $cm^{-1}$, 1380 to 1464 $cm^{-1}$ or 2731 to 2960 $cm^{-1}$ in a shift wavenumber from the excitation wavelength.

The second measured intraocular substance is lipid, and determination can be made through a spectral intensity of a fluorescent spectrum of 450 to 650 nm or an integrated value of a spectrum in a proper wavelength range within the range with respect to lecithin (phosphatidylcholine).

The third measured intraocular substance is bilirubin, and determination can be made through a Raman scattering peak at at 500 to 540 $cm^{-1}$, 670 to 710 $cm^{-1}$, 900 to 980 $cm^{-1}$, 1220 to 1300 $cm^{-1}$, 1310 to 1330 $cm^{-1}$, 1400 to 1500 $cm^{-1}$ or 1550 to 1670 $cm^{-1}$ in a shift wavenumber from the excitation wavelength.

The fourth measured intraocular substance is glycated protein, and determination can be made through a spectral intensity of a fluorescent spectrum of 640 to 850 nm or an integrated value of a spectrum in a proper wavelength range within the range with respect to glycated albumin.

The fifth measured intraocular substance is an AGE (advanced glycated end product). The AGE can also be similarly measured and determined. The AGE, called a late stage product, is a product in a late stage of such nonenzymic saccharification reaction (glycation) that an amino group of amino acid, peptide or protein reacts with a carbonyl group of reducing sugar, and watched as a substance related to organopathy resulting from a diabetic chronic complication.

The sixth measured intraocular substance is saccharified crystallin. Saccharified crystallin can also be similarly measured and determined.

These intraocular substances are substances which are present in the body. A conventional method of measuring fluorescence from an eyeball is performed after injecting fluorescein-Na into a vein. The present invention can also be utilized as an apparatus for measuring such an externally injected fluorescent substance. To this end, the seventh measured intraocular substance is an externally injected fluorescent substance such as fluorescein-Na.

When the measured intraocular substances are at least two types of substances among sugar, lipid, bilirubin, glycated protein, an AGE, saccharified crystallin and the like, peak intensities or peak areas of Raman scattered light components of shift wavenumbers selected for these substances, spectral intensities of fluorescence, or integrated values of proper wavelength ranges are employed, so that measured values of the respective substances can be obtained from these plurality of measured values by multivariate regression analysis.

The multivariate regression analysis operation is adapted to make data analysis through multivariate regression analysis such as principal component regression analysis (PCR) or a partial least square method (PLS method). In the multivariate regression analysis, regression analysis can be made by employing a number of spectral intensities at once, whereby quantitative analysis of higher accuracy as compared with single regression analysis is possible. While multiple regression analysis is most generally employed, a number of samples are required and its quantitative analysis accuracy is reduced if correlation between spectral intensities at respective shift wavenumbers is high. On the other hand, PCR which is multivariate regression analysis can intensify spectral intensities at a plurality of shift wavenumber regions to principal components which are irrelevant to each other and delete unnecessary noise data, whereby high quantitative analysis accuracy can be attained. Further, the PLS method can also utilize data of sample concentration in extraction of principal components, whereby high quantitative analysis accuracy can be attained similarly to the PCR. As to the multivariate regression analysis, "Tahenryo Kaiseki" (by Kazuo Nakatani, Shinyo-Sha) can be referred to.

In order to draw out necessary information from a spectrum complexity fluctuating by various fluctuation factors, data processing by a computer is remarkably useful. A typical processing method is stored in processing software provided in a commercially available near infrared apparatus or the like. As commercially available software, there is Unscramber by CAMO Company or the like. The typical processing method is the aforementioned multiple regression analysis, PLS, the principal component regression analysis or the like.

Large streams of data processing which is applied to quantitative regression analysis by multivariate regression analysis are (1) formation of a calibration model (calibration curve), (2) evaluation of the calibration model, and (3) determination of an unknown sample.

In order to perform calibration, it is necessary to measure a proper number of samples for forming a calibration curve in sufficient accuracy. Obtained spectra are subjected to preprocesses at need. Typical preprocesses are smoothing, differentiation and normalization of the spectra, which are general processes.

The calibration is processing of constructing mathematical relational expressions between spectral data and analytical values of target characteristics, i.e., models. Formation of models is performed by a statistical technique by employing analytical values of samples for forming a calibration curve and spectral data.

In order to correctly evaluate accuracy of prediction of the prepared calibration curve with respect to an unknown sample, measurement errors with respect to the unknown sample are obtained through an evaluation sample. When the accuracy of the calibration curve is decided as being insufficient, the type of the processing method or parameters are changed at need, to correct the calibration curve.

A calibration curve which is recognized as having sufficient accuracy is employed as a relational expression for predicting values of target characteristics from spectral data in analysis of the unknown sample, to be used for determination of the unknown sample concentration.

According to the present invention, the excitation optical system and the photoreceiving optical system are so arranged as to be capable of detecting scattered light or fluorescence from the cornea while distinguishing the same from those from other eyeball portions, whereby the intraocular substances can be measured on the basis of optical information from the cornea, and information useful for diagnosing diabetes mellitus or another disease etc. can be noninvasively obtained.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIGS. 5A, 5B and 5C, illustrating a further embodiment integrating optical systems into a boggle structure, are a plan view showing arrangement of the optical systems in the interior, a side elevational view on a photoreceiving optical system side showing the arrangement of the optical systems in the interior, and a perspective view as viewed from the eyeball side respectively;

DESCRIPTION OF THE PREFERRED EMBODIMENTS

Figure 1:
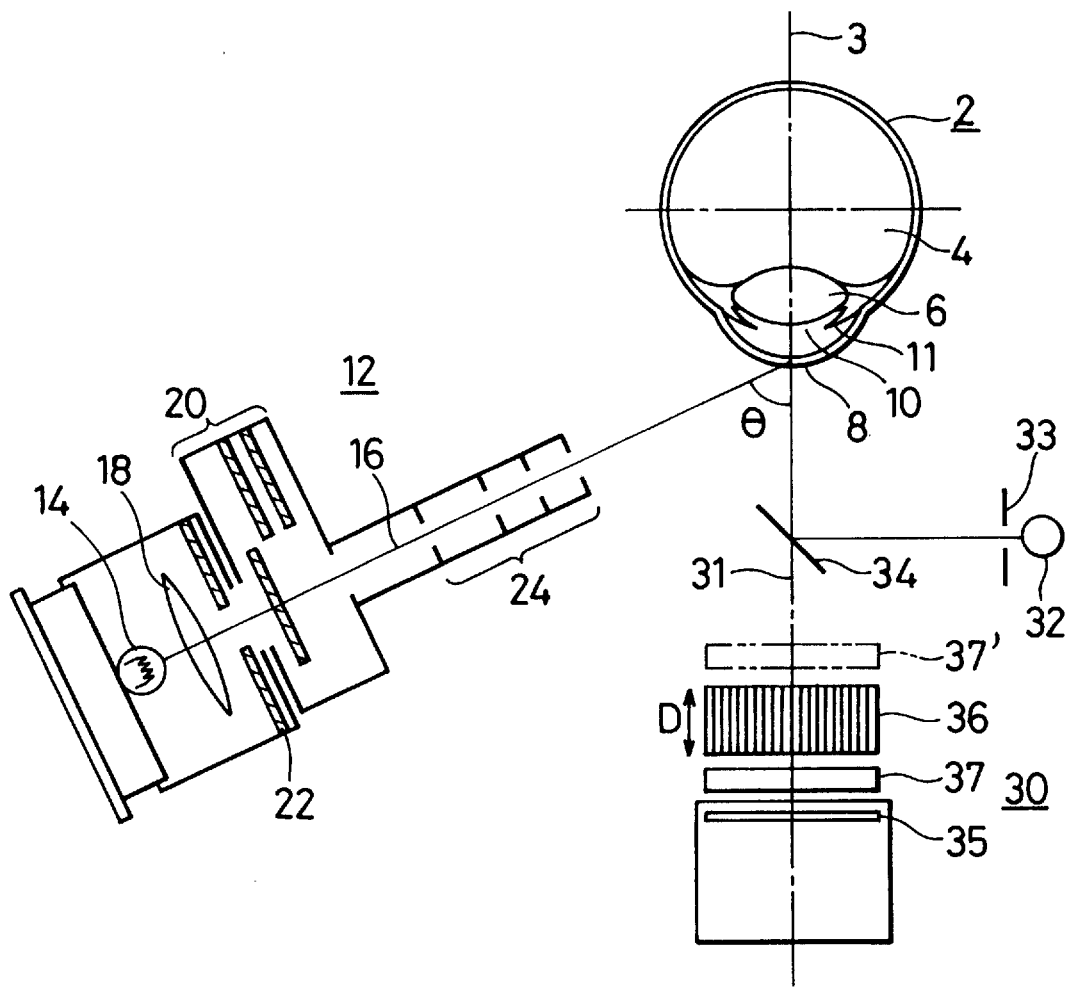
FIG. 1 is a plan sectional view schematically showing an embodiment.

FIG. 1 schematically illustrates an embodiment. Numeral 2 denotes an eyeball, having a crystalline lens 6 provided in front of a vitreous body 4 and a cornea 8 provided on the frontmost part. A clearance between the crystalline lens 6 and the cornea 8 is filled up with aqueous humor 10 which is a transparent liquid. An iris 11 is present between the crystalline lens 6 and the cornea 8, and a central opening of the iris 11 is the pupil. Numeral 3 denotes an ocular axis.

An excitation optical system 12 comprises an incandescent lamp such as a tungsten lamp as a light source 14, and a lens 18 for condensing excitation light generated from the light source 14 and optical filters 20 for fetching a narrow wavelength range from the excitation light and monochromating the same are provided on an optical axis 16 of the excitation optical system 12. A plurality of, three in the figure, optical filters 20 are so arranged that the same can be switched in response to a desired excitation beam wavelength An excitation light beam is adjusted to a narrow parallel beam of 0.1 to 2 mm in diameter by a slit 22 provided between the optical filters 20 and the lens 18 and a plurality of slits 24 provided on an outgoing side beyond the optical filters 20.

On the other hand, an optical axis 31 of a photoreceiving optical system 30 is spatially different from the optical axis 16 of the excitation optical system 12, and arranged on a position intersecting with the optical axis 16 of the excitation optical system 12 on the cornea 8. An angle θ formed by the optical axes 16 and 31 of the excitation and photoreceiving optical systems 12 and 30 is so set that no excitation light beam is incident upon the crystalline lens 6 through the pupil, and when the eyeball 2 is so fixed that the ocular axis 3 is coincident with the optical axis 31 of the photoreceiving optical system 30, the angle θ is 40° to 90°. Referring to FIG. 1, θ is 45°.

In order to fix the ocular axis 3 to be coincident with the optical axis 31 of the photoreceiving optical system 30, an optical system comprising a light source 32 for generating visible light, a slit 33 for converting light from the light source to a narrow beam, and a half mirror 34 for placing the beam adjusted by the slit 33 on the optical axis 31 and introducing the same into the eyeball 2 is provided.

In the photoreceiving optical system 30, a one- dimensional solid-state image pickup device 35 such as a CCD sensor or a photodiode array is arranged on its optical axis 31 as a photodetector. The one-dimensional solid-state image pickup device 35 comprises a line of CCD photoelectric conversion element arrangement, the direction of which is along a straight line perpendicular to the optical axis 31 of the photoreceiving optical system 30 in a plane including the optical axes 16 and 31 of the excitation and photoreceiving optical systems 12 and 30. The pitch of the photoelectric conversion element arrangement of the one-dimensional solid-state image pickup device 35 is 125 μm, for example.

On a light incidence side of the one-dimensional solid-state image pickup device 35, a slit 36 is arranged as an optical device which can distinguish measuring light generated from the cornea 8 from that generated from other eyeball portions and introduce the same into the one-dimensional solid-state image pickup device 35. The slit 36, which is prepared by arranging a plurality of thin plates in a direction parallel to the optical axis 31 of the photoreceiving optical system 30 and perpendicular to the plane including the optical axes 16 and 31 of the excitation and photoreceiving optical systems 12 and 30 in a direction perpendicular to the optical axis 31 of the photoreceiving optical system 30 in the plane including the optical axes 16 and 31 of the excitation and photoreceiving optical systems 12 and 30, associates a position where the plane including the optical axes 16 and 31 of the excitation and photoreceiving optical systems 12 and 30 intersects with the eyeball 2 with the positions of the photoelectric conversion elements of the one- dimensional solid-state image pickup device 35. The pitch of the slit 36 preferably corresponds to the photoelectric conversion element pitch of the one-dimensional solid- state image pickup device 35, and the depth D of the slit 36 is 5 to 30 mm.

Spectroscopic means 37 such as an FT, a filter or an AOTF is arranged between the slit 36 and the one- dimensional solid-state image pickup device 35, so that the measuring light from the eyeball 2 can be separated into its spectral components. Alternatively, the spectroscopic means 37 such as an FT, a filter or an AOTF may be arranged on a measuring light incidence side upon the slit 36, as shown by numeral 37.

The operation of the embodiment shown in FIG. 1 is described. The excitation light beam is incident upon the aqueous humor 10 through the cornea 8. Only a component of measuring light of scattered light and fluorescence generated from the cornea 8 and the aqueous humor 10 which is parallel to the optical axis 31 is transmitted through the slit 36, and separated into its spectral components through the spectroscopic means 37 and incident upon the one- dimensional solid-state image pickup device 35. The positions of the photoelectric conversion elements of the one-dimensional solid-state image pickup device 35 correspond to a measuring light generation position at the eyeball 2 due to the slit 36, so that it is possible to identify from which position the information is generated. In particular, a detection signal from a CCD photoelectric conversion element on the optical axis 31 includes information which is related to the scattered light and the fluorescence generated from the cornea 8 and important for measurement of intraocular substances. A detection signal from a CCD photoelectric conversion element in another place includes scattered light and fluorescence from the aqueous humor 10.

A diffraction grating can also be employed as the spectroscopic means 37. In case of measuring light from a single point on the cornea 8 by the slit 36, light transmitted through the slit 36 is guided to the diffraction grating to be wavelength-dispersed, and the one-dimensional solid-state image pickup device 35 is arranged so that the photoelectric conversion elements are arranged on the dispersion direction, whereby a polychromator is defined so that the light from the single point on the cornea 8 can be separated into its spectral components and simultaneously detected over a number of wavelengths.

In case of employing a two-dimensional solid-state image pickup device as the photodetector, a multi-channel spectroscope can be employed as the spectroscopic means 37. In this case, a line of measuring light incident upon the spectroscope through the slit 36 corresponds to a position on the eyeball 2. Wavelength dispersion is made in a direction perpendicular to an arrangement direction of the measuring light incident upon the spectroscope, whereby measuring light components from a plurality of positions on the eyeball 2 can be simultaneously separated into spectral components thereof and simultaneously detected over respective multiple wavelengths.

Figure 2:
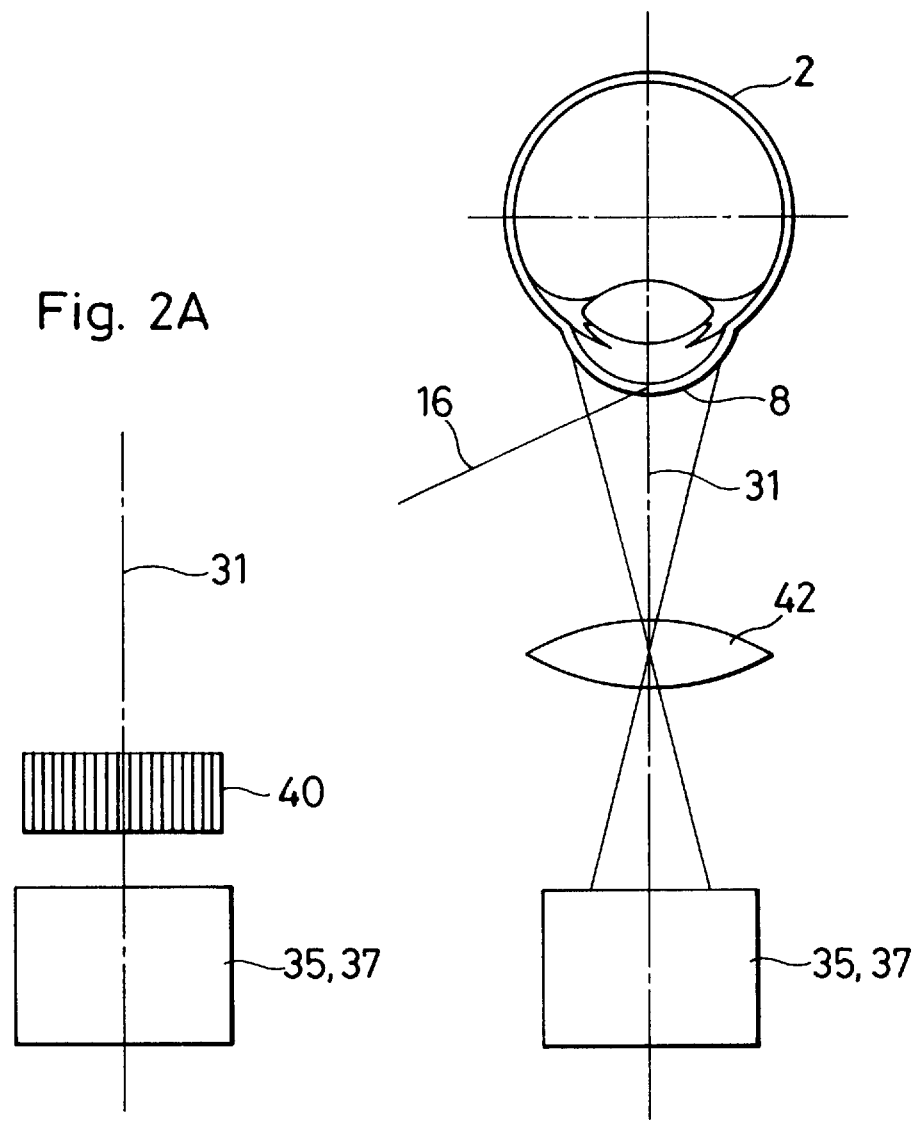
FIGS. 2A and 2B are plan sectional views schematically showing optical devices employing an optical fiber lens array and a lens in place of a slit 36 in the embodiment respectively.

FIGS. 2A and 2B illustrate other examples for substituting for the slit 36 shown in FIG. 1, as optical devices which can distinguish measuring light generated from corneas from that generated from other eyeball portions and introduce the same into photodetectors. FIG. 2A shows that employing an optical fiber lens array 40, and the pitch of its optical fiber member also preferably corresponds to the photoelectric conversion element pitch of a one-dimensional solid-state image pickup device 35. FIG. 2B shows that employing a lens 42. An image on a cornea 8 is formed on a one-dimensional solid-state image pickup device 35 by the lens 42, and measuring light generating positions on the cornea 8 and aqueous humor are arranged in opposite directions on the one-dimensional solid-state image pickup device 35.

As the photodetector of the photoreceiving optical system, the one-dimensional solid-state image pickup device 35 can be replaced with a photodiode consisting of a single photoelectric conversion element.

Figure 3:
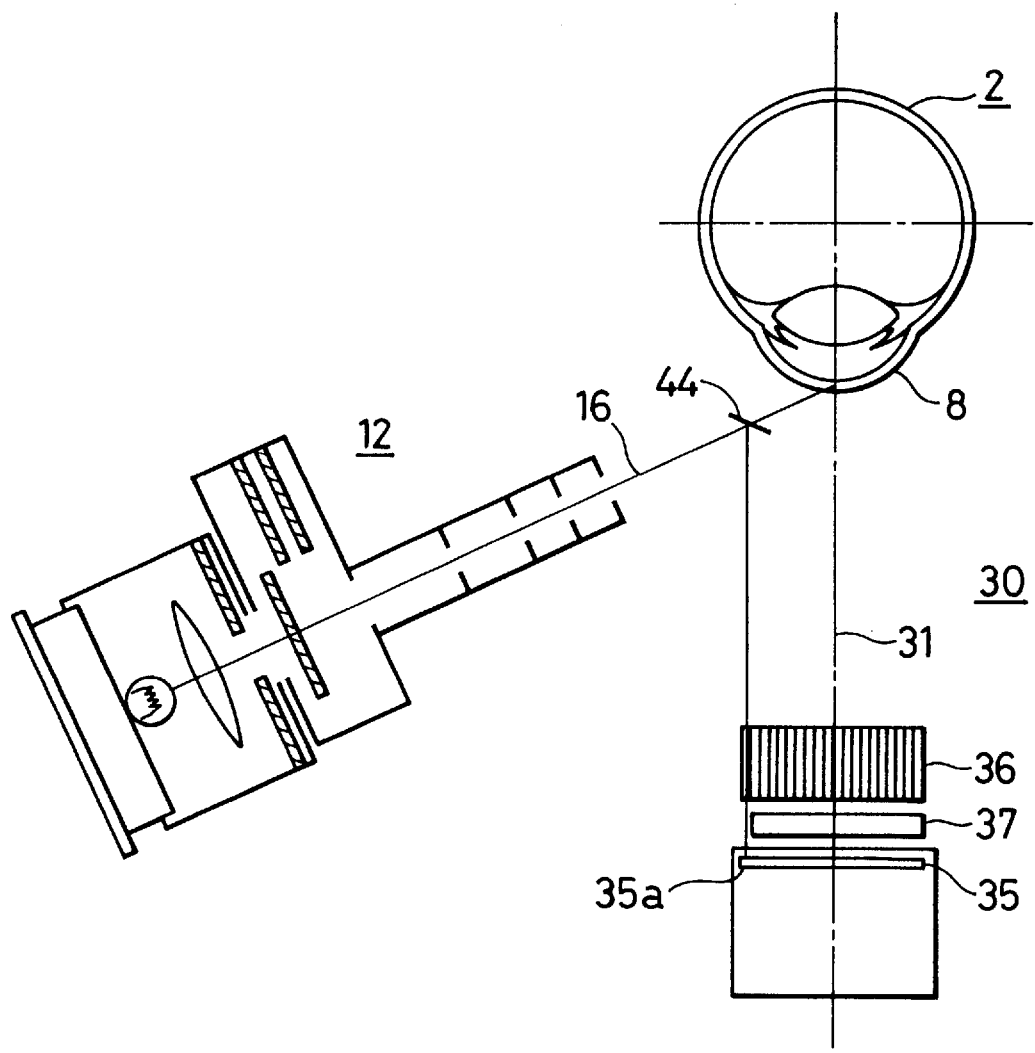
FIG. 3 is a plan sectional view schematically showing another embodiment comprising means for correcting fluctuation of a light source intensity.

FIG. 3 illustrates an embodiment comprising means for correcting fluctuation of a light source intensity. A half mirror 44 is arranged on an optical axis 16 of an excitation optical system 12, so that part of excitation light is directly incident upon a partial photoelectric conversion element 35a of a one-dimensional solid-state image pickup device 35. A detection signal from a cornea or another portion received by a photoelectric conversion element in another portion of the one-dimensional solid- state image pickup device 35 is divided by a detection signal of the photoelectric conversion element 35a receiving the excitation light beam and normalized, whereby fluctuation of the light source intensity can be corrected so that a correct measured value is obtained.

Figure 4:
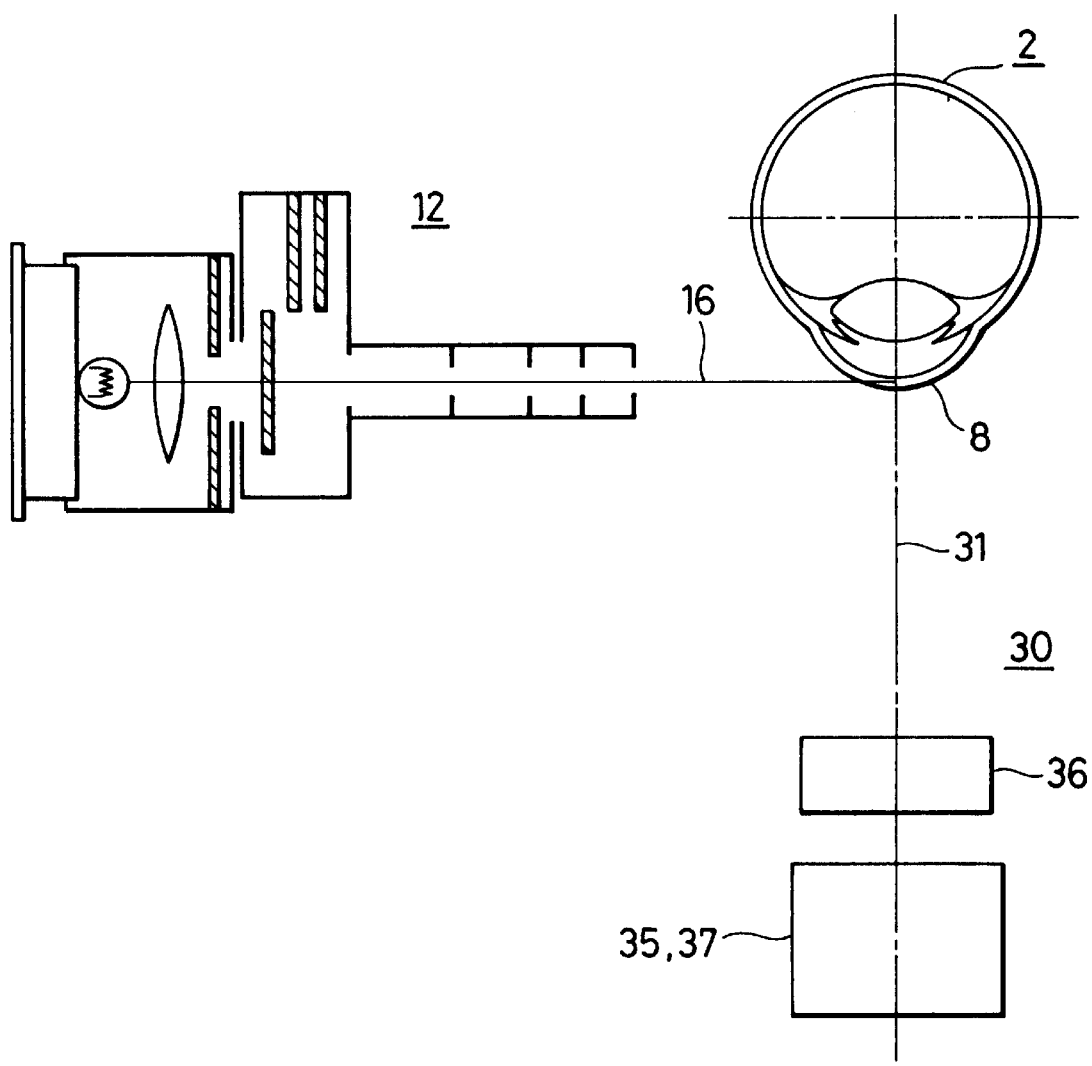
FIG. 4 is a plan sectional view showing still another embodiment setting an angle formed by optical axes of an excitation optical system and a photoreceiving optical system at 90°.

Referring to FIG. 4, the angle θ formed by the optical axes 16 and 31 of the excitation and photoreceiving optical systems 12 and 30 in the embodiment shown in FIG. 1 is set at 90°. In this case, only the cornea 8 can be irradiated with the excitation light beam, so that the photoreceiving optical system 30 can obtain only the information from the cornea 8 by receiving only the measuring light such as scattered light and fluorescence from the cornea 8.

FIGS. 5A, 5B and 5C, illustrating a further embodiment integrating the present invention into a goggle structure, are a plan view showing arrangement of optical systems in the interior, a side elevational view on a photoreceiving optical system side showing the arrangement of the optical systems in the interior, and a perspective view as viewed from the eyeball side respectively. An excitation optical system 12 and a photoreceiving optical system 30 such as those shown in FIGS. 1 to 4 are arranged in a goggle structure 50. A semiconductor laser which is effective for miniaturization is employed in the excitation optical system 12 as an excitation light source. Further, the goggle structure also comprises a transmission circuit for driving the light source and a photodetector and transmitting a signal detected by the photodetector to the exterior or the like. A control part 52 includes such a driving part or the transmission circuit.

FIGS. 6 to 13 show exemplary Raman scattering and fluorescence spectra of intraocular substances to be measured in the present invention. In each figure, the excitation light is an He-Ne laser beam of 632.8 $\mu$m.

Figure 6:
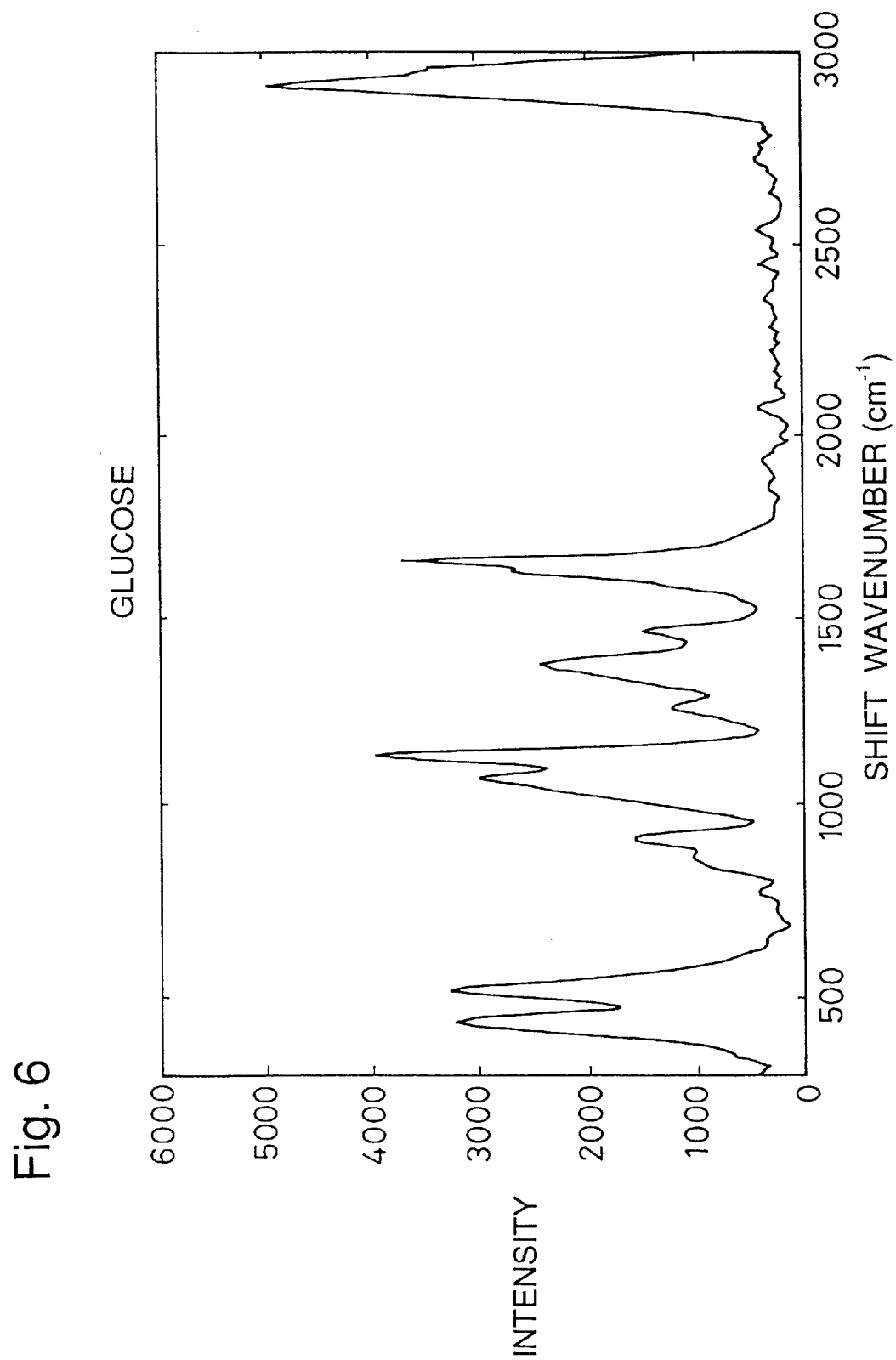
FIG. 6 illustrates a Raman scattering spectrum of glucose.

FIG. 6 shows a Raman scattering spectrum of glucose, which is provided with peaks at positions of 420 to 450 $cm^{-1}$, 460 to 550 $cm^{-1}$, 750 to 800 $cm^{-1}$, 850 to 940 $cm^{-1}$, 1000 to 1090 $cm^{-1}$, 1090 to 1170 $cm^{-1}$, 1200 to 1300 $cm^{-1}$, 1300 to 1390 $cm^{-1}$, 1400 to 1500 $cm^{-1}$ and 2850 to 3000 $cm^{-1}$ in shift wavenumbers from an excitation wavelength. Central wavenumbers of these peaks are 438 $cm^{-1}$, 530 $cm^{-1}$, 776 $cm^{-1}$, 917 $cm^{-1}$, 1087 $cm^{-1}$, 1103 $cm^1$, 1298 $cm^{-1}$, 1373 $cm^{-1}$, 1461 $cm^{-1}$ and 2907 $cm^{-1}$.

Figure 7:
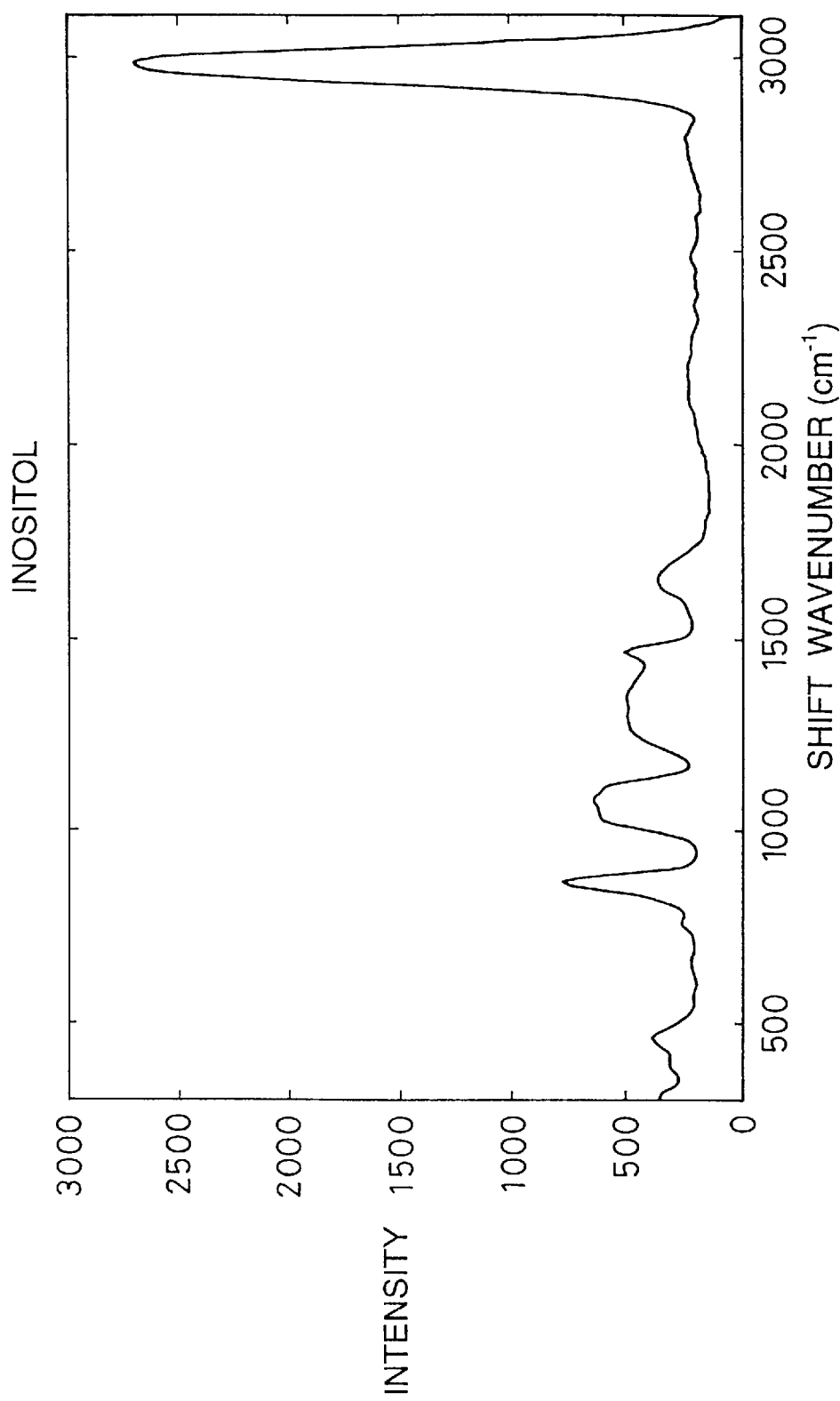
FIG. 7 illustrates a Raman scattering spectrum of inositol.

FIG. 7 shows a Raman scattering spectrum of inositol, which is provided with peaks at positions of 400 to 500 $cm^{-1}$, 700 to 900 $cm^{-1}$, 1000 to 1100 $cm^{-1}$, 1200 to 1500 $cm^{-1}$ and 2900 to 3050 $cm^{-1}$ in shift wavenumbers from the excitation wavelength Central wavenumbers of these peaks are 443.852 $cm^{-1}$, 864.743 $cm^{-1}$, 1074.37 $cm^{-1}$, 1468.06 $cm^{-1}$ and 2995.59 $cm^{-1}$.

Figure 8:
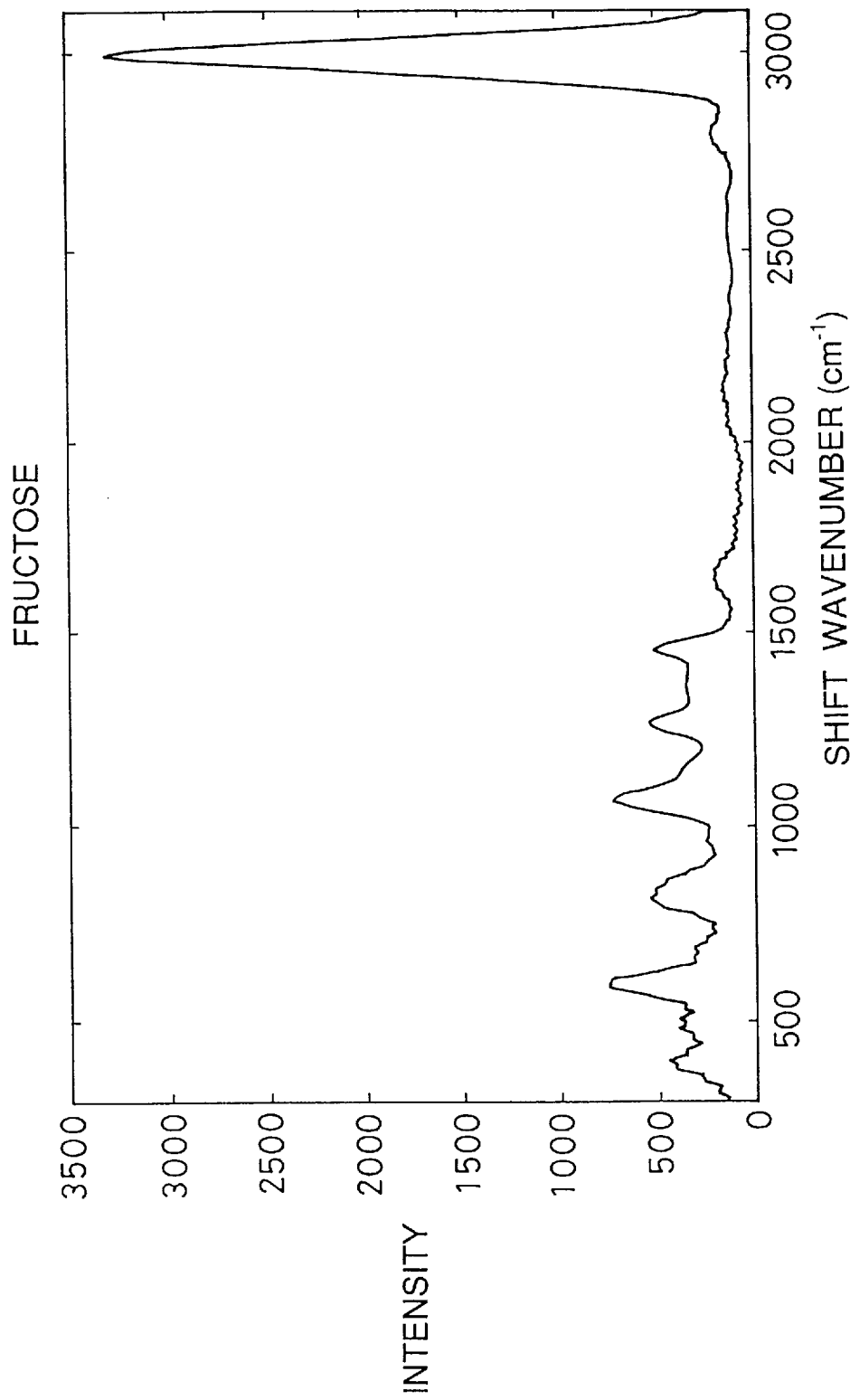
FIG. 8 illustrates a Raman scattering spectrum of fructose.

FIG. 8 shows a Raman scattering spectrum of fructose, which is provided with peaks at positions of 550 to 620 $cm^{-1}$, 650 to 700 $cm^{-1}$, 780 to 870 $cm^{-1}$, 900 to 980 $cm^{-1}$, 1000 to 1150 $cm^{-1}$, 1200 to 1300 $cm^{-1}$, 1400 to 1480 $cm^{-1}$ and 2900 to 3050 $cm^{-1}$ in shift wavenumbers from the excitation wavelength. Central wavenumbers of these peaks are 599.093 $cm^{-1}$, 688.482 $cm^{-1}$, 802.175 $cm^{-1}$, 963.9821 $cm^{-1}$, 1074.37 $cm^{-1}$, 1267.38 $cm^{-1}$, 1468.0621 $cm^{-1}$ and 2995.59 $cm^{-1}$.

Figure 9:
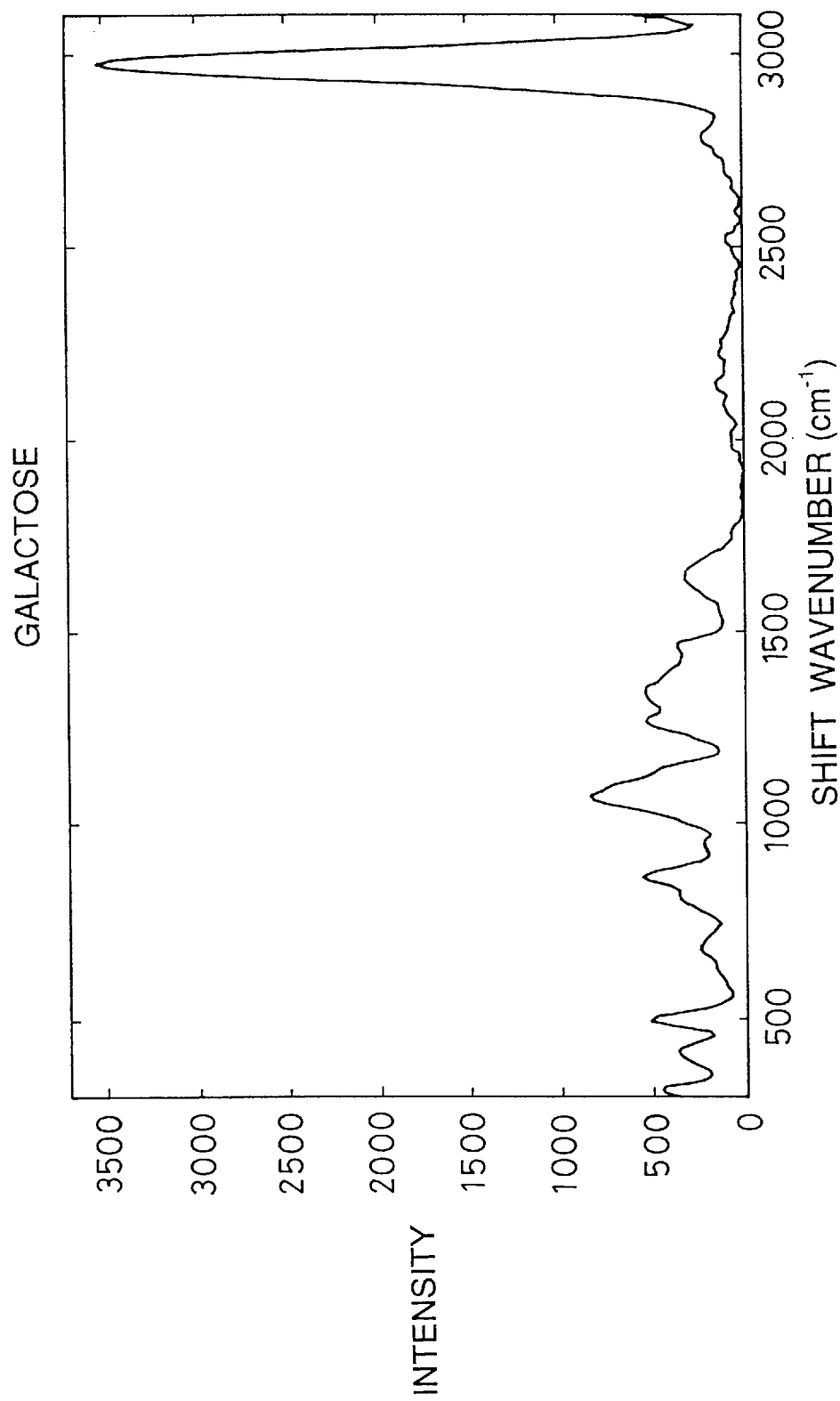
FIG. 9 illustrates a Raman scattering spectrum of galactose.

FIG. 9 shows a Raman scattering spectrum of galactose, which is provided with peaks at positions of 450 to 550 $cm^{-1}$, 630 to 900 $cm^{-1}$, 1000 to 1180 $cm^{-1}$, 1200 to 1290 $cm^{-1}$, 1300 to 1380 $cm^{-1}$, 1400 to 1500 $cm^{-1}$ and 2850 to 3050 $cm^{-1}$ in shift wavenumbers from the excitation wavelength. Central wavenumbers of these peaks are 495.884 $cm^{-1}$, 864.743 $cm^{-1}$, 1062.17 $cm^{-1}$, 1267.38 $cm^{-1}$, 1362.38 $cm^{-1}$, 1468.06 $cm^{-1}$ and 2976.02 $cm^{-1}$.

Figure 10:
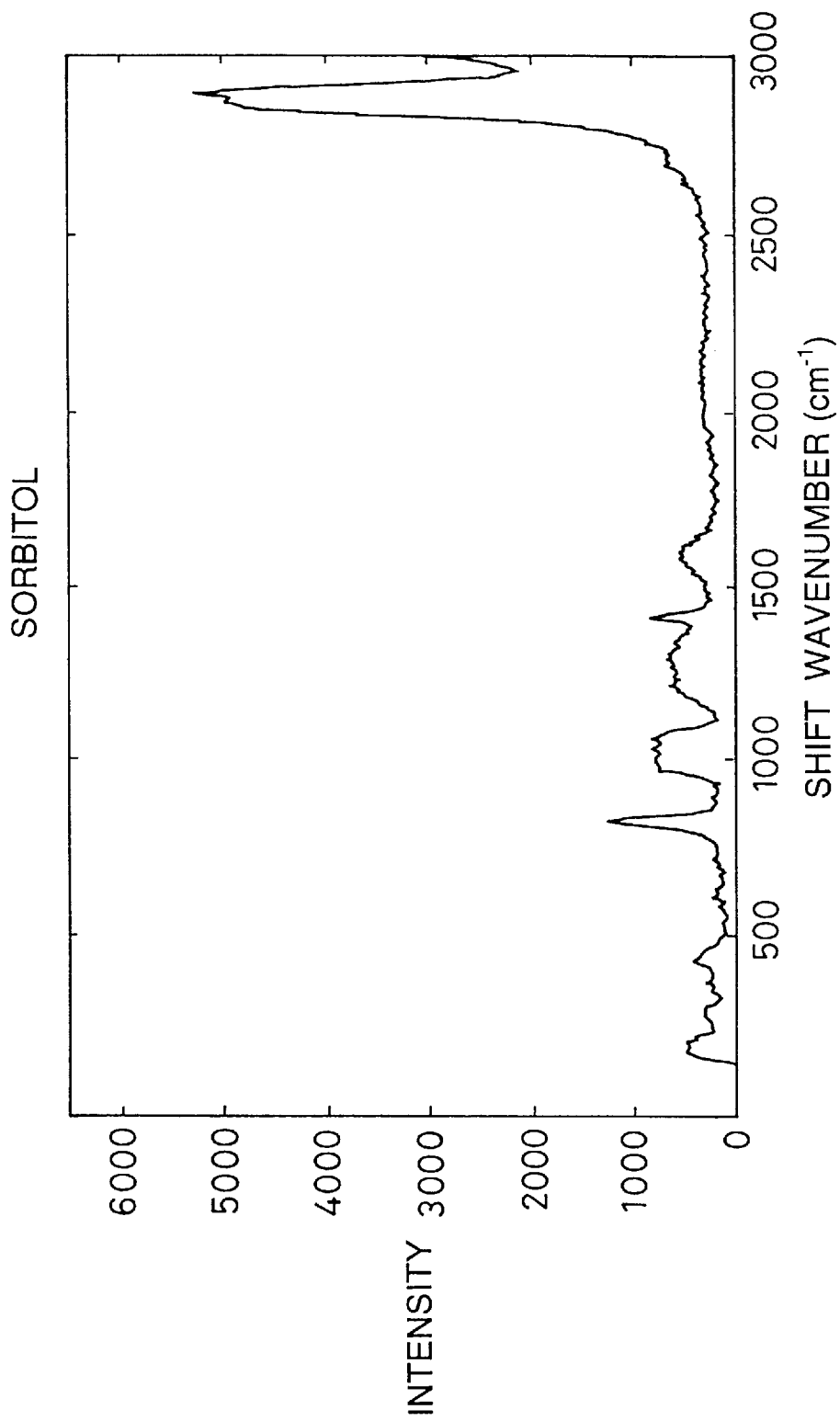
FIG. 10 illustrates a Raman scattering spectrum of sorbitol.

FIG. 10 shows a Raman scattering spectrum of sorbitol, which is provided with peaks at positions of 388 to 488 $cm^{-1}$, 749 to 862 $cm^{-1}$, 933 to 1120 $cm^{-1}$, 1380 to 1464 $cm^{-1}$ and 2731 to 2960 $cm^{-1}$ in shift wavenumbers from the excitation wavelength Central wavenumbers of these peaks are 438 $cm^{-1}$, 821 $cm^{-1}$, 1414 $cm^{-1}$, nearby 1600 $cm^{-1}$ and 2893 $cm^{-1}$.

Figure 11:
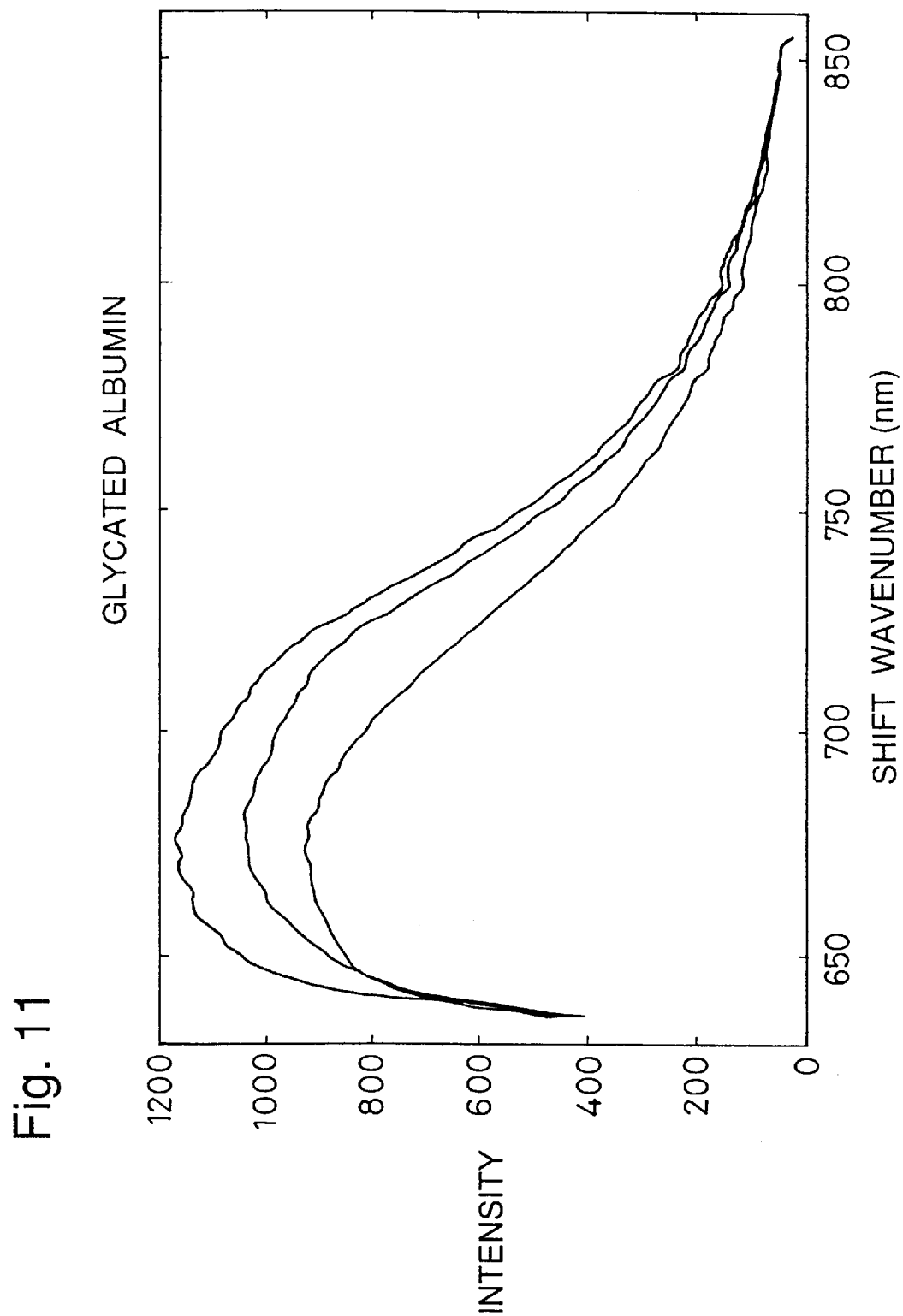
FIG. 11 illustrates a Raman scattering spectrum of glycated albumin.

FIG. 11 shows a fluorescence spectra of glycated albumin, which has a peak at 640 to 850nm. Aqueous solution samples having concentrations of 61.6%, 33.3% and 24.8% are measured, and spectral intensities are increased as the concentrations are increased.

Figure 12:
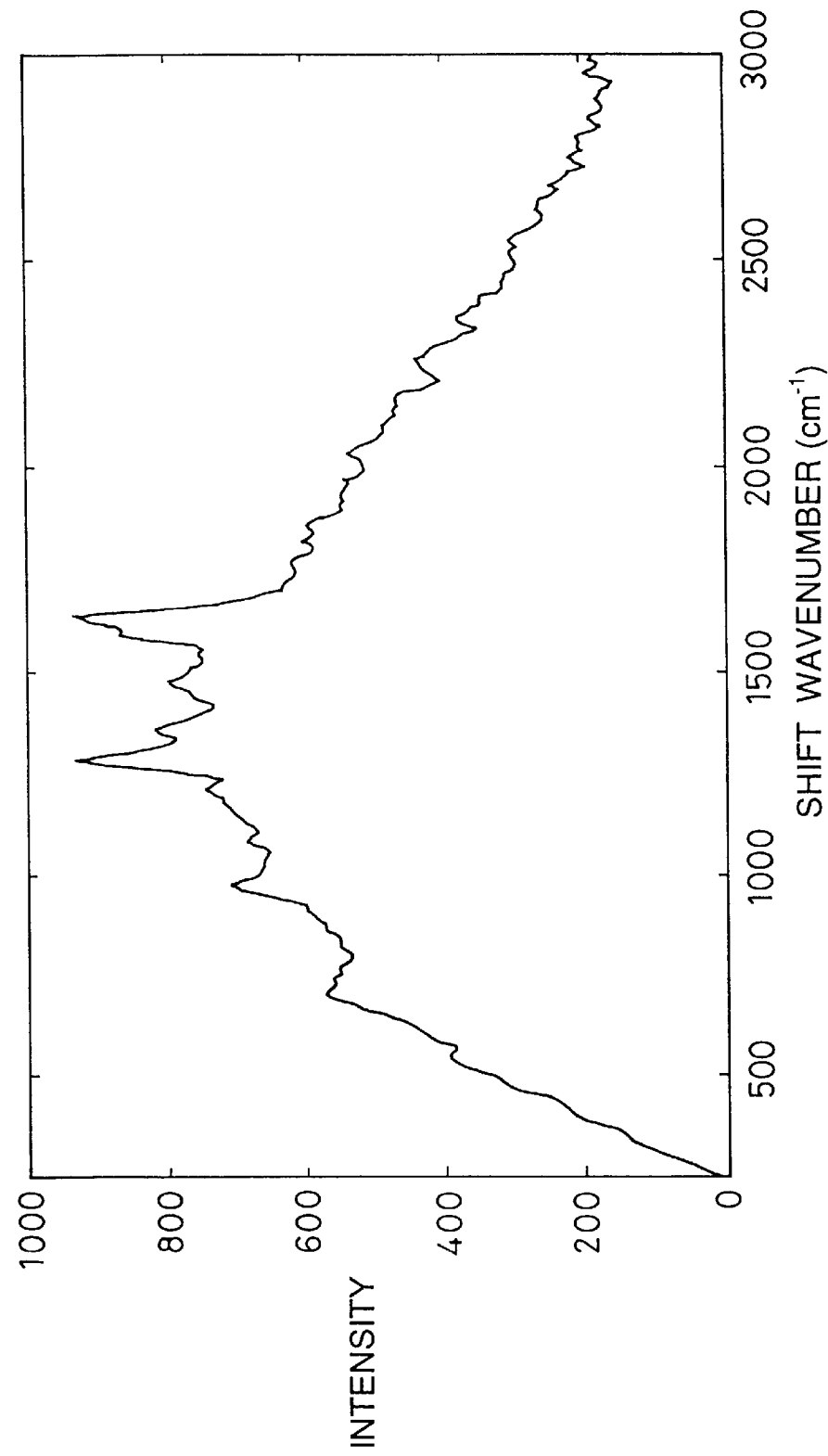
FIG. 12 illustrates a Raman scattering spectrum of ditaurobilirubin.

FIG. 12 shows a Raman scattering spectrum of ditaurobilirubin, which is provided with peaks at positions of 500 to 540 $cm^{-1}$, 670 to 710 $cm^{-1}$, 900 to 980 $cm^{-1}$, 1220 to 1300 $cm^{-1}$, 1310 to 1330 $cm^{-1}$, 1400 to 1500 $cm^{-1}$ and 1550 to 1670 $cm^{-1}$ in shift wavenumbers from an excitation wavelength Central wavenumbers of these peaks are 520 $cm^{-1}$, 688 $cm^{-1}$, 940 $cm^{-1}$, 1250 $cm^{-1}$, 1320 $cm^{-1}$, 1445 $cm^{-1}$ and 1615 $cm^{-1}$.

Figure 13:
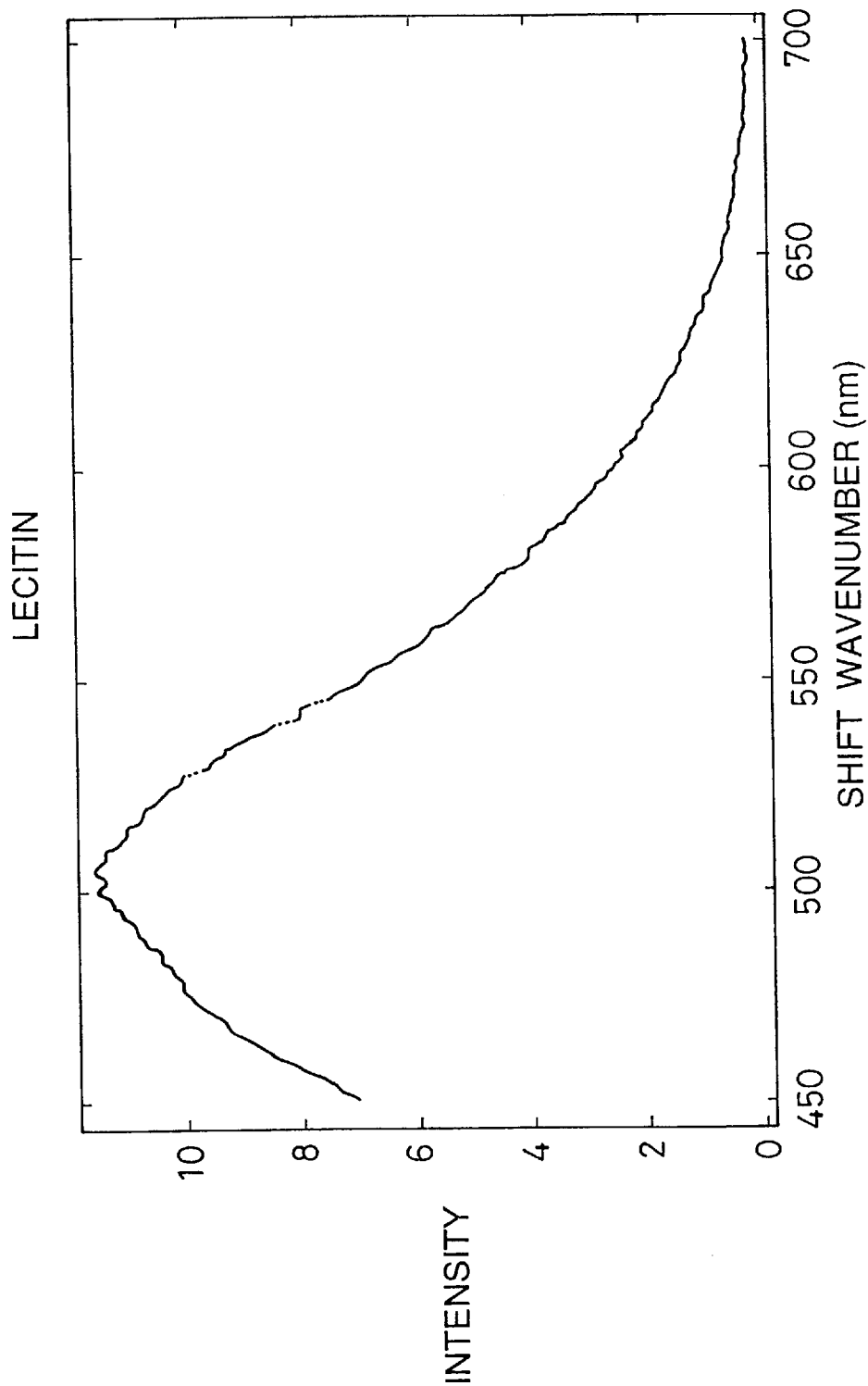
FIG. 13 illustrates a fluorescence spectrum of lecithin.

FIG. 13 shows a fluorescence spectrum of lecithin, which has a peak at 450 to 650 nm.

Although the present invention has been described and illustrated in detail, it is clearly understood that the same is by way of illustration and example only and is not to be taken by way of limitation, the spirit and scope of the present invention being limited only by the terms of the appended claims.

We claim:

1. An intraocular substance measuring apparatus for irradiating an eyeball with a monochromated or single-wavelength excitation light beam in the visible to near infrared regions from an excitation optical system and detecting measuring light including at least one of scattered light and fluorescence being emanated from said eyeball by a photoreceiving optical system, thereby measuring an intraocular substance, wherein said excitation optical system is arranged in such a positional relation that said excitation light beam is incident upon a cornea and not upon a crystalline lens, and said photoreceiving optical system has an ocular axis being spatially different from an optical axis of said excitation optical system, and comprises an optical device to guide said measuring light being emanated from said cornea and to distinguish the measuring light being emanated from said cornea from light being emanated from other eyeball portions, and a photodetector to detect said measuring light being guided by said optical device.

2. The intraocular substance measuring apparatus in accordance with claim 1, wherein said photoreceiving optical system further comprises a spectroscope to separate said measuring light being emanated from said eyeball into its spectral components, and wherein said photodetector detects said measuring light being separated into said spectral components by said spectroscope.

3. The intraocular substance measuring apparatus in accordance with claim 1, further comprising an ocular axis fixing light source, wherein said ocular axis fixing light source produces a light beam having an angle with respect to said optical axis of said photoreceiving optical system, and wherein said light beam stabilizes said ocular axis.

4. The intraocular substance measuring apparatus in accordance with claim 1, further comprising a two-dimensional solid-state image pickup device to detect a direction of said eyeball, for incorporating an output of said photodetector of said photoreceiving optical system while observing the direction of said eyeball with said two-dimensional solid-state image pickup device.

5. The intraocular substance measuring apparatus in accordance with claim 1, wherein said photodetector of said photoreceiving optical system is a two-dimensional solid-state image pickup device which detects a direction of said eyeball.

6. The intraocular substance measuring apparatus in accordance with claim 1, wherein said optical axis of said excitation optical system forms an angle of about 40° to 90° with said ocular axis of said photoreceiving optical system, and wherein said ocular axis is fixed in a measuring direction.

7. The intraocular substance measuring apparatus in accordance with claim 1, wherein said photodetector of said photoreceiving optical system is a solid-state image pickup device having a plurality of photoelectric conversion elements positioned in a linear series, said linear series forming an angle with said ocular axis of said photoreceiving optical system in a plane including said optical axis of said excitation optical system and said ocular axis of said photoreceiving optical system, and said optical device of said photoreceiving optical system associates a position where said plane intersects with said eyeball with positions of said photoelectric conversion elements of said solid-state image pickup device.

8. The intraocular substance measuring apparatus in accordance with claim 1, wherein said photodetector of said photoreceiving optical system is a single photoelectric conversion element positioned on said ocular axis of said photoreceiving optical system, and said optical device of said photoreceiving optical system selectively directs light being emanated from a point where said optical axis of said excitation optical system intersects with said ocular axis of said photoreceiving optical system on said cornea into said photodetector.

9. The intraocular substance measuring apparatus in accordance with claim 2, wherein said spectroscope is a Fourier transform spectroscope, a filter, or an acousto-optic tunable filter.

10. The intraocular substance measuring apparatus in accordance with claim 2, wherein said photodetector of said photoreceiving optical system is a one- or two-dimensional solid-state image pickup device, said optical device of said photoreceiving optical system selectively directs light being emanated from a point where said optical axis of said excitation optical system intersects with said ocular axis of said photoreceiving optical system on or near said cornea, and said spectroscope disperses said light into separate wavelengths in a photoelectric conversion element arrangement direction of said solid-state image pickup device.

11. The intraocular substance measuring apparatus in accordance with claim 1, wherein said excitation light beam is positioned parallel to said optical axis of said excitation optical system.

12. The intraocular substance measuring apparatus in accordance with claim 1, wherein said excitation optical system further comprises a condensing optical system to condense said excitation beam incident upon said cornea.

13. The intraocular substance measuring apparatus in accordance with claim 1, further comprising a beam splitter, said beam splitter being positioned on said optical axis of said excitation light beam of said excitation optical system, wherein said beam splitter separates a first portion of said excitation light and wherein said first portion of said excitation light is incident upon a photoelectric conversion element of said photodetector or a second photodetector to produce a first output of said photodetector, and wherein said first output is compared to a second output from a photoelectric conversion element of a photodetector receiving said measuring light from said eyeball.

14. The intraocular substance measuring apparatus in accordance with claim 1, wherein said excitation optical system and said photoreceiving optical system are housed in a goggle structure being attachable to a face.

15. The intraocular substance measuring apparatus in accordance with claim 14, wherein said goggle structure comprises a transmission circuit to output information detected by said photoreceiving optical system to an external data processor.

16. The intraocular substance measuring apparatus in accordance with claim 1, wherein said intraocular substance is a sugar, wherein said sugar is glucose, inositol, fructose, galactose, or sorbitol, and wherein determination is performed with respect to glucose through a Raman scattering peak at 420 to 1500 $cm^{-1}$ or 2850 to 3000 $cm^{-1}$ in a shift wavenumber from an excitation wavelength;

determination is performed with respect to inositol through a Raman scattering peak at 400 to 1500 $cm^{-1}$ or 2900 to 3050 $cm^{-1}$ in a shift wavenumber from said excitation wavelength;

determination is performed with respect to fructose through a Raman scattering peak at 550 to 1500 $cm^{-1}$ or 2900 to 3050 $cm^{-1}$ in a shift wavenumber from said excitation wavelength;

determination is performed with respect to galactose through a Raman scattering peak at 400 to 1500 or 2850 to 3050 $cm^{-1}$ in a shift wavenumber from said excitation wavelength; or determination is performed with respect to sorbitol through a Raman scattering peak at 380 to 1500 $cm^{-1}$ or 2700 to 2960 $cm^{-1}$ in a shift wavenumber from said excitation wavelength.

17. The intraocular substance measuring apparatus in accordance with claim 1, wherein said intraocular substance is a lipid, and determination is performed with respect to lecithin through a spectral intensity of a fluorescence spectrum in a wavelength range of 450 to 650 nm or an integrated value of a spectrum of a proper wavelength range within the range.

18. The intraocular substance measuring apparatus in accordance with claim 1, wherein said intraocular substance is bilirubin, and determination is performed through a Raman scattering peak at 500 to 540 $cm^{-1}$, 670 to 710 $cm^{-1}$, 900 to 980 $cm^{-1}$, 1220 to 1300 $cm^{-1}$, 1310 to 1330 $cm^{-1}$, 1400 to 1500 $cm^{-1}$ or 1550 to 1670 $cm^{-1}$ in a shift wavenumber from an excitation wavelength.

19. The intraocular substance measuring apparatus in accordance with claim 1, wherein said intraocular substance is a glycated protein, and determination is performed with respect to glycated albumin through a spectral intensity of a fluorescence spectrum in a wavelength range of 640 or 850 nm or an integrated value of a spectrum of a proper wavelength range within the range.

20. The intraocular substance measuring apparatus in accordance with claim 1, wherein said intraocular substance is an advanced glycated end product.

21. The intraocular substance measuring apparatus in accordance with claim 1, wherein said intraocular substance is a glycated crystallin.

22. The intraocular substance measuring apparatus in accordance with claim 1, wherein concentrations of at least two intraocular subtances are measured, said substances being a sugar, a lipid, bilirubin or a glycated protein, wherein peak intensities or peak areas of Raman scattered light of shift wavenumbers are selected for said intraocular substances, and wherein spectral intensities of fluorescence or integrated values of wavelength ranges are employed, so that measured values of said substances are obtained from a plurality of values by multivariate regression analysis.

23. The intraocular substance measuring apparatus in accordance with claim 1, wherein
said intraocular substance is an exogenous fluorescent substance.

24. The apparatus in accordance with claim 1, wherein
said intraocular substance is a sugar, said sugar being glucose, inositol, fructose, galactose, or sorbitol, and wherein
determination is performed with respect to glucose through a Raman scattering peak at 420to 450 cm$^{-1}$, 460 to 550 cm$^{-1}$, 750 to 800 cm$^{-1}$, 850 to 940 cm$^{-1}$, 1000 to 1090 cm$^{-1}$, 1090 to 1170 cm$^{-1}$, 1200 to 1300 cm$^{-1}$, 1300 to 1390 cm$^{-1}$, 1450 to 1500 cm$^{-1}$ or 2850 to 3000 cm$^{-1}$ in a shift wavenumber from an excitation wavelength;
determination is performed with respect to inositol through a Raman scattering peak at 400 to 500 cm$^{-1}$, 700 to 900 cm$^{-1}$, 1000 to 1100 cm$^{-1}$, 1200 to 1500 cm$^{-1}$ or 2900 to 3050 cm$^{-1}$ in a shift wavenumber from said excitation wavelength;
determination is performed with respect to fructose through a Raman scattering peak at 550 to 620 cm$^{1}$, 650 to 700 cm$^{-1}$, 780 to 870 cm$^{-1}$, 900 to 980 cm$^{-1}$, 1000 to 1150 cm$^{-1}$, 1200 to 1300 cm$^{-1}$, 1400 to 1480 cm$^{-1}$ or 2900 to 3050 cm$^{-1}$ in a shift wavenumber from said excitation wavelength;
determination is performed with respect to galactose through a Raman scattering peak at 450 to 550 cm$^{-1}$, 630 to 900 cm$^{-1}$, 1000 to 1180 cm$^{-1}$, 1200 to 1290 cm$^{-1}$, 1300 to 1380 cm$^{-1}$, 1400 to 1500 cm$^{-1}$ or 2850 to 3050 cm$^{-1}$ in a shift wavenumber from said excitation wavelength; or
determination is performed with respect to sorbitol through a Raman scattering peak at 388 to 488 cm$^{-1}$, 749 to 862 cm$^{-1}$, 933 to 1120 cm$^{-1}$, 1380 to 1464 cm$^{-1}$ or 2731 to 2960 cm$^{-1}$ in a shift wavenumber from said excitation wavelength.

25. Apparatus for determining concentration of an intraocular substance in an eyeball having a cornea and a crystalline lens, comprising:
an excitation optical system having a monochromated or single-wavelength excitation light beam, said excitation optical light system being positionable adjacent said eyeball that has said excitation light beam directed to be incident on the cornea but not the crystalline lens; and
a photoreceiving optical system having an optical guide device and a photodetector that is responsive to light of specific wavelengths to produce electric signals that are indicative of intensity of light of such specific wavelengths that are incident on said photodetector, said photoreceiving optical system also being positionable adjacent the eyeball where light emanated from the cornea is incident on said optical guide device and with said device being oriented in a manner that guides light being emanated from the cornea to said photodetector.

26. A method for determining concentration of a substance in a body of a subject, said method comprising:
(a) irradiating an eye of the subject with an excitation light beam, said excitation light beam being incident on a cornea but not on a crystalline lens of the eye to induce light emission from the cornea;
(b) passing a light emanated from the cornea through an optical element to guide said light emanated from the cornea to a photodetector that is responsive to light of specific wavelengths to produce electric signals that are indicative of spectral intensity of light of such specific wavelengths that are incident on said photodetector;
(c) measuring said electric signals as a measure of said spectral intensity; and
(d) calculating concentration of the substance as a function of said electrical signals.

27. The method of claim 26, wherein said excitation light beam is a monochromated or a single-wavelength light beam.

28. The method of claim 26, wherein said excitation light beam comprises visible or near infrared light.

29. The method of claim 26, wherein said optical element is a slit or an optical fiber lens array.

30. The method of claim 26, wherein said passing includes the step of traversing a plurality of thin plates, wherein each of said plates is positioned in an orientation parallel to said measuring light.

31. The method of claim 26, wherein said passing includes the step of traversing an array of optical fiber lens, wherein each of said optical fiber lens is positioned in an orientation parallel to said measuring light.

32. The method of claim 26, wherein said optical element is a conjugate optical system comprising a lens, wherein said lens images said measuring light being emanated from the cornea onto a photodetector.

33. The method of claim 26, wherein said light emanated from the cornea comprises scattered light or fluorescence.

34. The method of claim 26, wherein said light emanated from the cornea comprises fluorescence.

35. The method of claim 26, further comprising
separating said light emanated from the cornea into spectral components before measuring spectral intensity.

36. The method of claim 35, wherein said light emanated from the cornea through a spectroscope.

37. The method of claim 36, wherein said spectroscope includes a Fourier transform spectroscope.

38. The method of claim 36, wherein said spectroscope includes an optical filter.

39. The method of claim 36, wherein said spectroscope includes an acousto-optic turnable filter.

40. The method of claim 26, wherein said irradiating includes the step of splitting the excitation light beam into a first portion and a second portion, said first portion being incident upon a photodetector and said second portion being incident upon the cornea.

41. The method of claim 40, wherein said step of splitting the excitation light beam is performed using a half mirror positioned between an excitation light source and the eye.

42. The method of claim 26, further comprising stabilizing an ocular axis of a photoreceiving optical system, said photoreceiving optical system comprising the optical element and the photodetector.

43. The method of claim 42, wherein said stabilizing includes the steps of:
exposing the eye to visible light to stabilize the ocular axis between the eye and the photodetector, wherein the step of exposing includes the steps of
generating a beam of visible light, passing the beam of visible light through a slit to produce a narrow beam of light, focusing the narrow beam of light on a half mirror, and reflecting a portion of the narrow beam of light into the eye.

44. The method of claim 26, wherein said substance includes a sugar.

45. The method of claim 26, wherein said substance includes a lipid.

46. The method of claim 26, wherein said substance includes bilirubin.

47. The method of claim 26, wherein said substance includes a glycated protein.

48. The method of claim 26, wherein said photodetector includes an array of solid-state image pickup device having a plurality of photoelectric conversion elements.

49. The method of claim 48, wherein said array is one-dimensional.

50. The method of claim 48, wherein said array is two-dimensional.

* * * * *